US006270467B1

(12) United States Patent
Yee

(10) Patent No.: US 6,270,467 B1
(45) Date of Patent: Aug. 7, 2001

(54) APPARATUS, SYSTEM, AND METHOD FOR PREVENTING COMPUTER VISION SYNDROME

(76) Inventor: Richard W. Yee, 3402 Robinwood, Houston, TX (US) 77005

( * ) Notice: Subject to any disclaimer, the term of this patent is extended or adjusted under 35 U.S.C. 154(b) by 0 days.

(21) Appl. No.: 09/059,976

(22) Filed: Apr. 14, 1998

(51) Int. Cl.$^7$ .................................................. A61H 1/00
(52) U.S. Cl. ............................. 601/37; 348/61; 600/558
(58) Field of Search .............................. 600/558; 348/61; 345/112; 601/37; 424/427, 428

(56) References Cited

U.S. PATENT DOCUMENTS

| | | |
|---|---|---|
| D. 339,596 | 9/1993 | Kopfer . |
| 4,201,210 * | 5/1980 | Hughes et al. ........................ 424/428 |
| 4,659,197 | 4/1987 | Weinblatt . |
| 5,171,306 | 12/1992 | Vo . |
| 5,191,364 | 3/1993 | Kopfer . |
| 5,307,095 | 4/1994 | Ogura . |
| 5,333,009 | 7/1994 | Gell, Jr. et al. ......................... 348/61 |
| 5,368,582 | 11/1994 | Bertera . |
| 5,384,593 * | 1/1995 | Gell, Jr. et al. ......................... 348/61 |
| 5,406,074 | 4/1995 | Grisell .................................. 250/221 |
| 5,428,411 | 6/1995 | Kopfer . |
| 5,617,872 * | 4/1997 | Scinto et al. .......................... 600/558 |
| 5,625,380 | 4/1997 | Hansen . |
| 5,682,210 | 10/1997 | Weirich . |

FOREIGN PATENT DOCUMENTS

| | | | |
|---|---|---|---|
| WO9012470 | 10/1990 | (WO) ............................ | H04N/5/262 |
| PCT/US91/ 07761 | 4/1992 | (WO) . | |

OTHER PUBLICATIONS

Patent Absracts of Japan, vol. 098, No. 002, Jan. 30, 1998 (JP 09 276253 Oct. 28, 1997).
Patent Abstracts of Japan, vol. 098, No. 005, Apr. 30, 1993 (JP 10 011675 Jan. 16, 1998).
Patent Abstracts of Japan, vol. 097, No. 003, Apr. 30, 1993 (JP 08 314423 Nov. 29, 1996).

International Search Report forPCT/US99/08060 dated Jul. 26, 1999.

Lerman., "Prolonged Release Medication in the Treatment of Eye Disease," *Israel Journal of Medical Sciences*, vol. 8, No. 8–9, Aug.–Sep. 1972, pp. 1402–1405.

Jennifer Tanaka and Mark Rambler. Health, How Dry Am I, Newsweek Magazine, Dec. 8, 1997, p. 14.

* cited by examiner

*Primary Examiner*—George Manuel
(74) *Attorney, Agent, or Firm*—Baker Botts L.L.P.

(57) ABSTRACT

The present invention provides a system, apparatus, and method for preventing Computer Vision Syndrome (CVS) that addresses the various causes of CVS. To help maintain a proper preocular tear film the present invention provides a device to generate a blink reminder signal and a blink indicator, such as a light, a speaker, or a portion of a display monitor, to communicate the blink reminder signal to the computer user. The device may incorporate feedback devices such as a blink monitor, a temperature monitor, a humidity monitor, an elapsed time monitor, or a clock. The present invention also provides an eye enclosure that defines an enclosed area about the computer user's eye that is at least partially enclosed. The invention incorporates components aimed at optimizing the environment within the enclosed area. For example, air moisteners communicating with the enclosed area maintain a relatively high humidity within the enclosed area and reduce the evaporation of fluid from the eyes. The moistening fluid may be adapted to the particular needs of the individual and other conditions, such as temperature, may also be controlled. Also, the composition of the tear film may be manipulated using the moistening fluid or a small pellet placed in the cul de sac of the user's eye to help maintain a proper tear film or otherwise change the tear film characteristics.

55 Claims, 8 Drawing Sheets

APPARATUS, SYSTEM, AND METHOD FOR PREVENTING COMPUTER VISION SYNDROME

BACKGROUND OF THE INVENTION

1. Field of Invention

The present invention relates to the field of medical devices. More specifically, the invention relates to an apparatus, system, and method for preventing Computer Vision Syndrome (CVS) that uses a variety of components, each aimed at addressing the causes of CVS.

2. Related Art

Computers have become indispensable tools of the workplace and popular devices for work and entertainment in the home. Accordingly, millions of people, in the United States alone, spend much of their day working on or otherwise using a computer. The time spent at the computer may extend up to eight hours or, depending upon the user's professional demands, much longer in a single, continuous stretch of time. In 1992, approximately 10 million people sought treatment for vision problems associated with looking at a display monitor of a computer for extended periods of time. A more recent survey suggested that, of the approximately 70 million Americans working at computers and looking at the computer display monitors for extended periods, eighty-eight percent experience some form of ocular complaints.

The ocular complaints experienced by the computer users typically include intermittent blurring of vision, eye strain, eye fatigue, burning sensations, irritation, and dry eyes, among others. The most common of the ocular complaints include ocular fatigue and irritation which are major symptoms of dry eyes. Usually, the symptoms occur after the computer user begins using the computer and looking at the display monitor and the symptoms progressively worsen becoming more intense the harder and longer the person uses the computer. The condition of a person experiencing one or more of the ocular complaints as a result of operating a computer and looking at a computer monitor is generally referred to as "Computer Vision Syndrome" (CVS). CVS not only causes pain and discomfort to the individual, but also reduces overall efficiency by reducing the time that a person can effectively work and concentrate while using a computer. Thus, CVS represents a drain on productivity and serves to increase medical expenses associated with treating the ocular complaints.

In general, the ocular complaints associated with CVS typically relate to some refractive error and/or shortcomings of the environment that ultimately relates back to some instability of the ocular surface (i.e. the ocular surface epithelial cells and the preocular tear film). Many people have eye disorders that do not allow them to properly focus. Further, upon reaching about age forty, the muscles that control a person's ability to focus, or accommodate, are ordinarily unable to properly adjust the eye to allow accurate viewing of a computer display monitor. Thus, the strain placed on these muscles causes fatigue that leads to an eventual inability to properly focus and to intermittent blurring.

Normally, when the eye is open, the stability of the tear film is affected by the size of the exposed area of the ocular surface and the time that the ocular surface is exposed to the environment between blinks. Regardless of whether the tear film component is normal, eyelid blinking is essential to achieve adequate tear spread onto the entire ocular surface and, thus, to form a stable preocular tear film. The size and area of exposure of the ocular surface as well as the environment determine the extent of tear evaporation. Therefore, complete and frequent eyelid blinking is necessary to minimize the ocular surface exposure and the eyelid fissure and to provide adequate spreading of the preocular tear film.

However, when a person is in an attentive and concentrated state, the exposed ocular surface area during interblink intervals is enlarged and the blink rate is reduced. A person typically enters this attentive and concentrated state when, for example, working at a computer and looking at a display monitor, reading, driving, watching television, and looking through a microscope. Thus, the natural attentive and concentrated effort of the person using a computer tends to produce ocular fatigue.

One recent effort aimed at treating the symptoms of CVS simply uses eye drops to provide a better preocular tear film and reduce the associated ocular complaints. While somewhat effective at performing the function for which the eye drops are intended, the effort does not provide a solution that addresses the causes of CVS and does not provide a solution that helps a computer user avoid CVS altogether.

Thus, despite the use of the prior art features, there remains a need for an apparatus, system, and method that helps a computer user avoid CVS and that uses a variety of components, each aimed at addressing the causes of CVS.

SUMMARY OF THE INVENTION

To achieve such improvements, the present invention provides an apparatus, system, and method to help a computer user avoid Computer Vision Syndrome (CVS). In general, the invention provides a set of individual components which may be used individually or in combination and each of which is designed to address the various causes of CVS. Included among the components are devices directed at maintaining a proper preocular tear film and avoiding damage to the epithelial cells. The components include devices and methods for ensuring an adequate blink rate to provide an adequate spread of the preocular tear film and for controlling the environmental conditions about the eye, such as the humidity, to optimize the eye environment. Other components provide for magnification to aid eye accommodation, filtering of the air in the eye environment, adapting the air moisture content to the needs of the individual computer user, and monitoring and adjusting the temperature and/or humidity of the eye environment.

In one aspect, the present invention provides an apparatus for preventing computer vision syndrome in a computer user viewing a display monitor of a computer that comprises means for generating a blink reminder signal and means for indicating a blink reminder to the computer user in response to the blink reminder signal. The means for generating a blink reminder signal generally comprises the computer used by the computer user or a separate control member. The frequency of blink reminders may be a set predetermined time interval which may be, for example, about sixteen to twenty blinks per minute or a varying time interval. To better achieve an appropriate blink rate, the present invention preferably includes means for monitoring the computer user's blinks. The blink monitor is preferably an infrared detector or a light source (e.g photodiode) for reflecting light off the computer user's eye and a light sensor (e.g. phototransistor) for detecting the reflected light. In one embodiment, the light source is the computer display monitor. In this embodiment, the phototransistor may be mounted on top of the display monitor so that the computer user does not have to wear any hardware. The information gained by monitoring the computer user's blinks is then used by the signal generator to adjust the blink reminder signal as needed to provide an appropriate blink rate. Thus, the blink monitor is in communication with and adapted to provide feedback to the signal generator and the signal generator is adapted to adjust the blink reminder signal according to the computer user's blink rate in response to the feedback provided by the blink monitor.

The blink indicator may be a speaker adapted to produce an audible blink reminder which may be a simple beep, a tone, an audible voice, or virtually any other sound, such as a song. Alternatively, the blink reminder may comprise a visible indicator adapted to produce a visual blink reminder. Examples of visible indicators include a light or at least a portion of the display monitor of the computer. The visual blink reminder may be a conscience message or a subliminal message generated on the display monitor. Another type of blink indicator is an electro-stimulus member adapted to produce an electro-stimulus blink reminder that provides involuntary blinking by the computer user.

As previously mentioned, the signal generator is preferably adapted to vary the blink reminder signal so that the blink reminder varies in response to the variation of the blink reminder signal. Such a variation allows the device to adapt to the needs of the individual user. Typically, such variation would be in response to the feedback provided by the blink monitor. However, the blink reminder may also vary depending upon the external input from a temperature monitor, a humidity monitor, an elapsed time monitor, or a clock.

Another aspect of the invention is a method for preventing computer vision syndrome in a computer user viewing a display monitor of a computer that comprises the steps of generating a blink reminder signal and indicating a blink reminder to the computer user in response to the blink reminder signal. The method may include generation of a blink reminder signal that has a constant or varying time interval between the blink reminders. Preferably, the method includes the steps of monitoring the computer user's blinks and adjusting the blink reminder signal according to the computer user's blink rate to ensure that the computer user blinks at a proper rate. The blink reminder may be altered in a variety of ways. For example, the method may involve increasing the intensity or varying the type of the blink reminder the greater the computer user's blink rate varies from the proper blink rate.

To relay the blink reminder to the computer user, the method may include the steps of indicating the blink reminder on the display monitor, providing a subliminal blink reminder, indicating the blink reminder by way of an audible blink reminder, and/or indicating the blink reminder by way of an electro-stimulus blink reminder.

An additional aspect of the invention provides an apparatus for preventing computer vision syndrome in a computer user viewing a display monitor of a computer that comprises an eye enclosure adapted to provide an enclosed area about the computer user's eyes that is at least partially enclosed, but may also be fully enclosed, from a surrounding environment without obstructing the computer user's vision of the display monitor and means for supporting and maintaining the eye enclosure in position on the computer user. The device may include means for moistening the enclosed area.

One embodiment for the air moistener comprises a nebulizer attached to the eye enclosure that is in fluid communication with the enclosed area and is adapted to provide a supply of nebulized moistening fluid to the enclosed area. Another embodiment comprises a moistening fluid or substance applied to the computer user's eyes so that the eyes act as a fluid supply reservoir and the moistening fluid evaporating from the computer user's eyes moistens the enclosed area. This embodiment may further comprise a moistening fluid supply, a pump member in fluid communication with the moistening fluid supply, and a fluid communication line in fluid communication with the pump member. The communication line is positioned and adapted to direct the moistening fluid to the computer user's eyes; and the pump member is adapted to pump the moistening fluid from the moistening fluid supply, through the communication line, and to the computer user's eyes. A third embodiment for the air moistener comprises a moistening fluid supply of moistening fluid in fluid communication with the enclosed area. The moistening fluid supply is adapted to permit evaporation of the moistening fluid from the moistening fluid supply to the enclosed area. Two embodiments for the moistening fluid supply include an open reservoir and a liquid permeable member adapted to absorb the moistening fluid and permit evaporation therefrom.

In one embodiment, the apparatus includes a pellet that is sized and adapted to fit within the cul de sac of the computer user's eye. The pellet is adapted to dissolve into the computer user's tear film and alter its characteristics. One manner in which the pellet may alter the tear film characteristics is that the pellet may increase the absorptive and decrease the evaporative characteristics of the tear film. The pellet may release a hyperosmotic substance, a preservative free aqueous, an ocular oil, and/or a goblet cell secreting agent among other substances.

The device may incorporate means for monitoring the temperature of the enclosed area and means for adjusting the temperature of the enclosed area that is adapted to maintain a predetermined temperature in the enclosed area. Likewise the device may incorporate means for monitoring the humidity of the enclosed area and means for adjusting the humidity of the enclosed area that is adapted to maintain a predetermined humidity in the enclosed area.

The moistening fluid may be adapted to the individual needs of the computer user by providing a preservative free aqueous, a goblet cell secreting agent (such as bromhexine), or ocular oil to the enclosed area as needed. The moistening fluid preferably has colligative properties that increase the absorptive and reduce the evaporative characteristics of the tear film.

In an alternative embodiment, the device includes a filter member attached to the enclosure in fluid communication with the enclosed area and the surrounding environment. Preferably the filter member is a sub-micron filter, such as a high efficiency particulate accumulator (HEPA) filter.

Additionally, the device may include a lens member, which may be tinted, attached to the enclosure that is adapted and positioned to provide magnification of images seen by the computer user's eyes. Thus, the strain imposed by accommodation is reduced.

To allow the user to use prescription glasses in connection with the eye enclosure, in one embodiment, the eye enclosure is sized and adapted to fit over a pair of spectacles worn by the computer user.

Yet another aspect of the present invention provides a method for preventing computer vision syndrome in a computer user viewing a display monitor of a computer that comprises the steps of providing an eye enclosure adapted to provide an enclosed area about the computer user's eyes that is at least partially enclosed, but that alternatively may be fully enclosed, without obstructing the computer user's vision of the display monitor and supporting and maintaining the eye enclosure in position on the computer user. Preferably the method includes the steps of moistening the enclosed area.

One embodiment for moistening the enclosed area comprises nebulizing a moistening fluid and spraying the nebulized moistening fluid into the enclosed area. Another embodiment involves applying a moistening fluid to the computer user's eye and allowing the moistening fluid to evaporate from the computer user's eye. A third embodiment comprises providing a moistening fluid supply of a moistening fluid in communication with the enclosed area that is adapted to permit evaporation of the moistening fluid from the moistening fluid supply to the enclosed area and allowing the moistening fluid to evaporate from the moistening fluid supply. The method may alternatively include the step of placing a pellet (having the above-described characteristics) in the computer user's eye and/or increasing the absorptive and decreasing the evaporative characteristics of the computer user's preocular tear film.

Alternative embodiments for the method include monitoring the temperature of the enclosed area and adjusting the temperature of the enclosed area to maintain a predetermined temperature and/or monitoring the humidity of the enclosed area and adjusting the humidity of the enclosed area to maintain a predetermined humidity. The method may further comprise adapting a moistening fluid to the specific needs of the computer user and using the moistening fluid to moisten the enclosed area. Such adaptation of the moistening fluid preferably comprises using a preservative free aqueous as the moistening fluid for the computer user suffering from aqueous deficiency, applying a goblet cell secreting agent (such as bromhexine) as the moistening fluid for the computer user suffering from mucin deficiency, and applying an ocular oil as the moistening fluid for the computer user suffering from lipid deficiency.

Other alternative embodiments include the steps of filtering the air entering the enclosed area and/or reducing the light entering the computer user's eye by tinting the eye enclosure.

Still another aspect of the present invention provides a system for preventing computer vision syndrome in a computer user viewing a display monitor of a computer that comprises an eye enclosure adapted to provide an enclosed area about the computer user's eyes that is at least partially enclosed from a surrounding environment without obstructing the computer user's vision of the display monitor, means for supporting and maintaining the eye enclosure in position on the computer user, means for moistening the enclosed area, means for generating a blink reminder signal, and means for indicating a blink reminder to the computer user in response to the blink reminder signal.

Other components and methods for preventing CVS are discussed herein and include medication and/or massage of the facial muscles and proper positioning of the computer monitor among others.

BRIEF DESCRIPTION OF THE DRAWINGS

The manner in which these objectives and other desirable characteristics can be obtained is explained in the following description and attached drawings in which.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention generally provides an apparatus, system, and method to help a computer user avoid Computer Vision Syndrome (CVS). In general, the invention provides a set of individual components which may be used individually or in combination and each of which is designed to address the various causes of CVS. Included among the components are devices directed at maintaining a proper preocular tear film and avoiding damage to the epithelial cells. The components include devices and methods for ensuring an adequate blink rate to provide an adequate spread of the preocular tear film and for controlling the environmental conditions about the eye, such as the humidity, to optimize the eye environment. Other components provide for magnification to aid eye accommodation, filtering of the air in the eye environment, adapting the air moisture content to the needs of the individual computer user, and monitoring and adjusting the temperature and/or humidity of the eye environment. Additional, components will be discussed throughout the following description.

Figure 1:
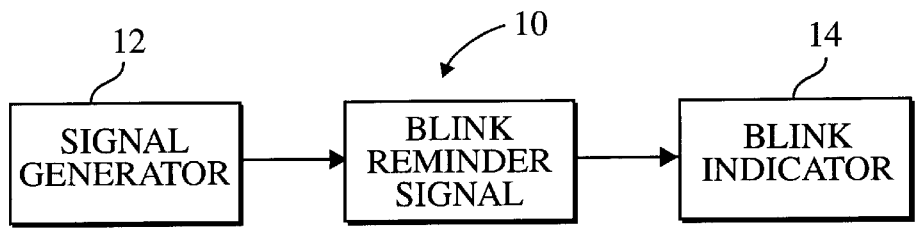
FIG. 1 is a schematic diagram of one aspect of the present invention.
Figure 7:
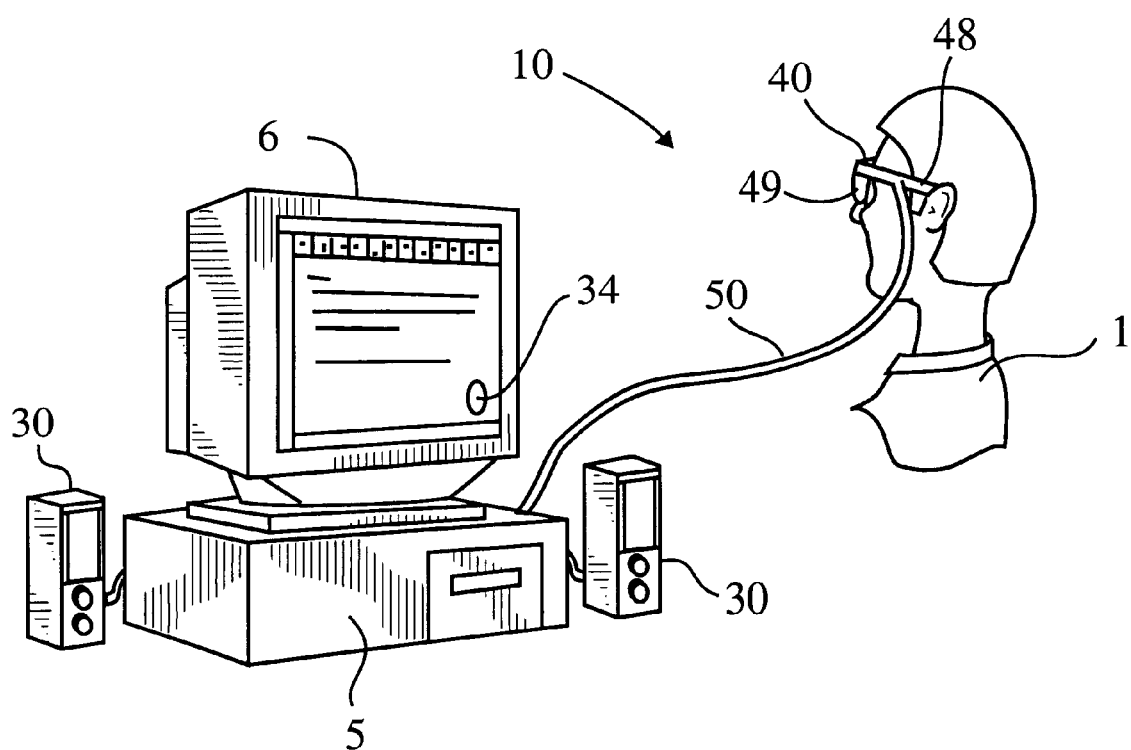
FIG. 7 is a partial perspective view of a computer user using a computer and viewing a display monitor.
Figure 8:
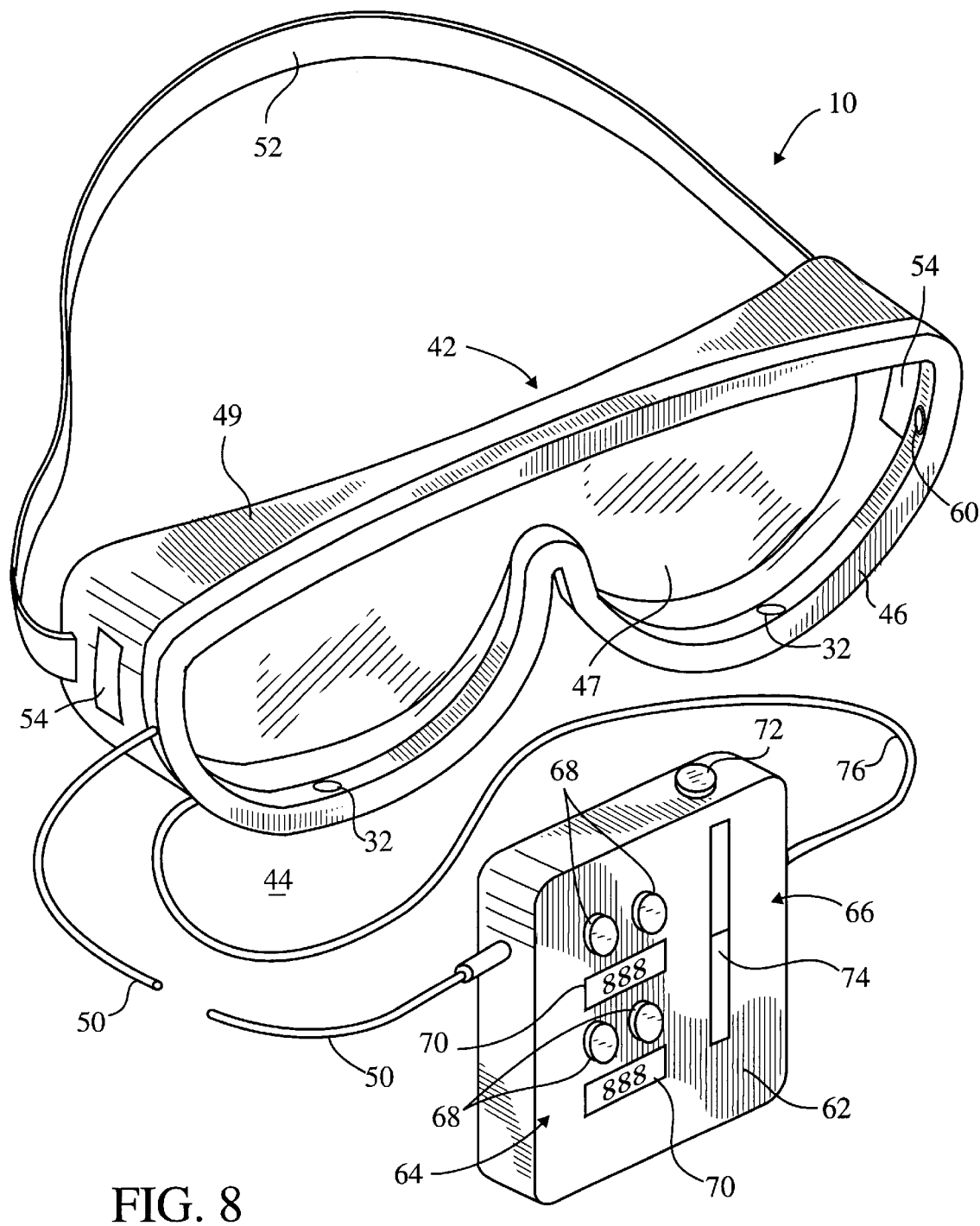
FIG. 8 is a perspective view of an eye enclosure connected to a portable base unit.

One aspect of the invention, shown in FIGS. 1, 7 and 8, provides means for generating a blink reminder signal (also referred to herein as the "signal generator") 12 and means for indicating a blink reminder to a computer user 1 in response to the blink reminder signal (also referred to herein as the "blink indicator") 14 which may take a variety of forms. For example, these components may be passive and provide a steady reminder regardless of any actual blinking by the computer user 1 or active and take into account the actual blinking by the computer user 1 or other factors.

In general, the signal generator 12 is a control member 64. The control member 64 is adapted to provide the blink reminder signal which is preferably an electrical impulse. The control member 64 may be the computer 5 in use by the computer user 1 containing software programmed to produce the desired blink reminder. Alternatively, the control member 64 may comprise a separate microprocessor or an electrical circuit designed to produce the desired blink reminder. In the case of a separate control member 64, the power source may comprise any known power source commonly used for electronic devices. Although non-electronic control members 64 and blink reminders (erg. a metronome) are anticipated and specifically incorporated herein, the preferred embodiment uses an electronic device as previously discussed.

In a passive type device, the frequency of the blink reminder signal is a predetermined time interval, for example, between about sixteen and twenty blinks per minute. In such a device, no feedback is required and the device simply produces a metronome-type signal of electrical impulses. The amplitude or other characteristics of the blink reminder signal may be varied as desired to provide for variation of the blink reminder to the computer user 1. Although specific variations of the blink indicator 14 are further discussed below, varying the blink reminder to the computer user 1 may provide a better reminder in that the changes may better get the attention of the computer user 1. Further, even in a passive type device, the frequency of the blink reminder signal may vary to better maintain the attention of the computer user 1.

Figure 2:
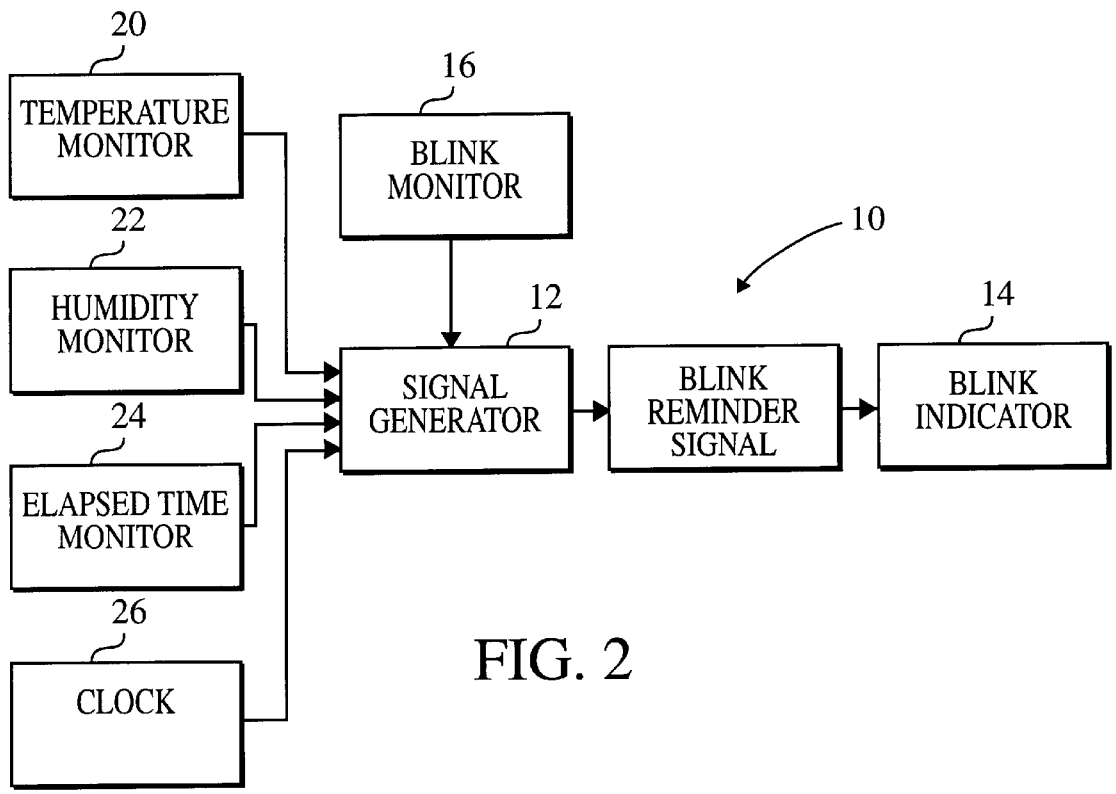
FIG. 2 is a schematic diagram of one aspect of the present invention incorporating external input devices.

FIG. 2 is a schematic diagram of an alternative preferred embodiment of an active type device for providing a blink reminder to a computer user 1. As shown in FIG. 2, the signal generator 12 is adapted to receive input from one or more external sources. Based upon the input provided by the external sources, the device 10 adjusts the blink reminder signal to provide a blink reminder signal optimized for the computer user 1. For example, the frequency, amplitude, or other characteristics of the blink reminder signal may be varied to provide the desired blink reminder.

Figures 3A, 3B:
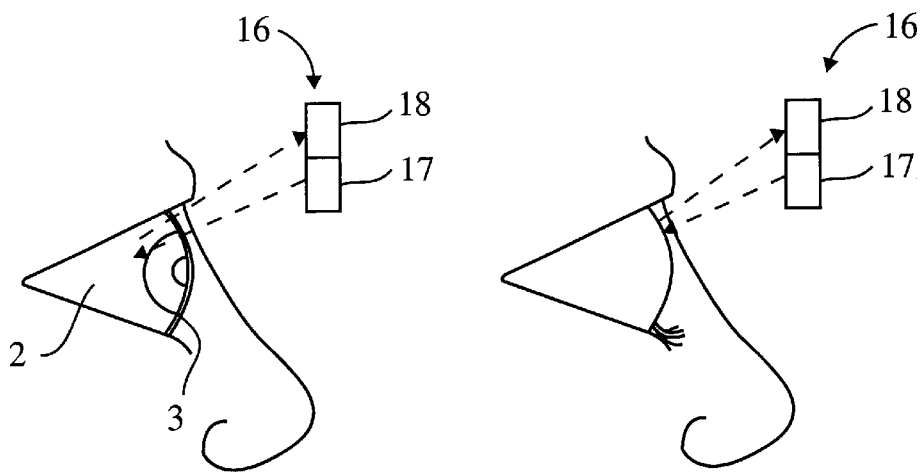
FIGS. 3A and 3B are schematic views showing the operation of a blink monitor.

One type of external monitoring and input source is a means for monitoring the computer user's blinks (also referred to herein as the "blink monitor") 16. The blink monitor 16 monitors the frequency of the computer user's blinks, the time between blinks, the time since the last blink, and the like. The signal generator 12 may then use this information in generating the blink reminder signal to adjust the blink reminder as needed to ensure adequate and proper blinking frequency (e.g. to maintain a preferred blink rate of, for example, between about sixteen and twenty blinks per minute). The blink monitor 16 may take a number of different forms. For example, as shown in FIGS. 3A and 3B, the blink monitor 16 may comprise a pair of photodiodes 17 (or "light sources") and a pair of phototransistors 18 (or "light detectors"). Each of the photodiodes 17 emits a small beam of light that strikes each of the computer user's eyes 2. When the incident light beams strike the large white sclera of the eyes 2 strong reflective light beams will return, with the reflected light beams striking the phototransistors 18. However, when the eyes 2 close to blink, the light reflected to the phototransistors 18 is relatively less. The phototransistors 18 may then signal the control member 64, or signal generator 12, that the computer user 1 has blinked.

Other embodiments may be used to detect blinks by the computer user 1. For example, the photodiodes 17 and phototransistors 18 may be replaced with infrared transmitters and detectors (a "infrared detector") or with some other type of light transmitter and detector device which are essentially variations of the previously described blink monitor 16. One such device capable of detecting the computer user's blinks is disclosed in U.S. Pat. No. 4,659, 197 issued to Weinblatt on Apr. 21, 1987 which is hereby incorporated by reference herein.

Figure 4:
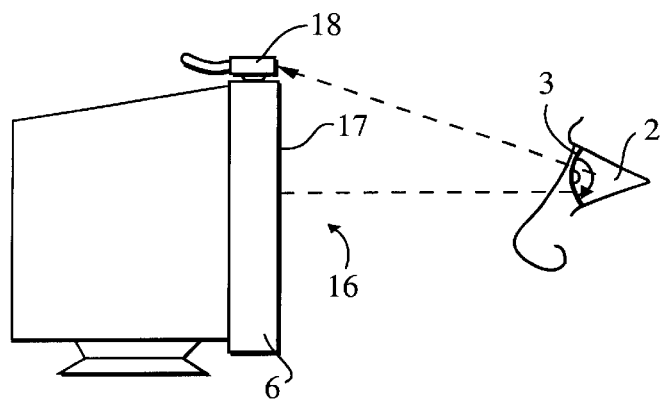
FIG. 4 is a side schematic view showing the light produced by the display monitor reflecting from the computer user's eye to the phototransistor mounted on top of the display monitor.

FIG. 4 is a schematic view showing a blink monitor 16 wherein the photodiode 17 comprises the display monitor 6. As shown in the figure, the light from the display monitor 6 strikes the computer user's eyes 2 and is reflected back toward the display monitor 6. A phototransistor 18 positioned on the display monitor measures the intensity of the reflected light and, thereby, detects computer user blinks. Accordingly, the computer user 1 need not wear any hardware to accommodate the blink monitor 16. The photodiode 17 may comprise essentially any light source and the phototransistor 18 may be remotely mounted from the computer user's eyes 2 so that the possible configurations of the blink monitor 16 are numerous.

By monitoring the blink rate of the computer user 1, the device 10 may adjust the blink reminder to provide a different frequency of blink reminders, different types of blink reminders, blink reminders of different intensities, or other blink reminder variations. In this way, the device 10 can help to ensure proper blinking and help to maintain a proper preocular tear film 3 on the eye 2 and, thereby, reduce or eliminate some of the primary causes of CVS.

As shown in FIG. 2, 3, 4 and 7 additional monitoring and input sources communicating with the blink generator may include means for monitoring the temperature, humidity, or elapsed time that the computer user 1 has been operating the computer 5 or other relevant times. Depending upon the temperature and humidity of the environment to which the computer user's eyes 2 are exposed, the evaporation of the tear film 3 from the eye 2 may vary. Thus, for example, in a very dry or hot climate, the computer user 1 may need to blink more often to maintain a proper preocular tear film 3 due to increased evaporation. Therefore, a temperature monitor 20 and a humidity monitor 22 may provide important feedback to the signal generator 12 that allows the signal generator 12 to adjust the frequency of the blink reminder signal to optimize the blinking of the computer user 1. The various means for measuring temperature (e.g. thermometers, thermocouples) and humidity (e.g hygrometers) are well known and any suitable temperature or humidity measurement devices are acceptable for use herewith.

Likewise, an elapsed time monitor 24 allows the signal generator 12 to increase the frequency of the blink reminders the longer the computer user 1 works. Typically, the symptoms of CVS increase the longer the computer user 1 views a display monitor 6. Accordingly, the computer user 1 may need to blink more often the longer the computer 5 is used. Similarly, the device 10 may incorporate a clock 26 in communication with the signal generator 12. The signal generator 12 may then increase the blink reminder frequency later in the day when most computer users have been awake and working or reading longer.

Figure 5:
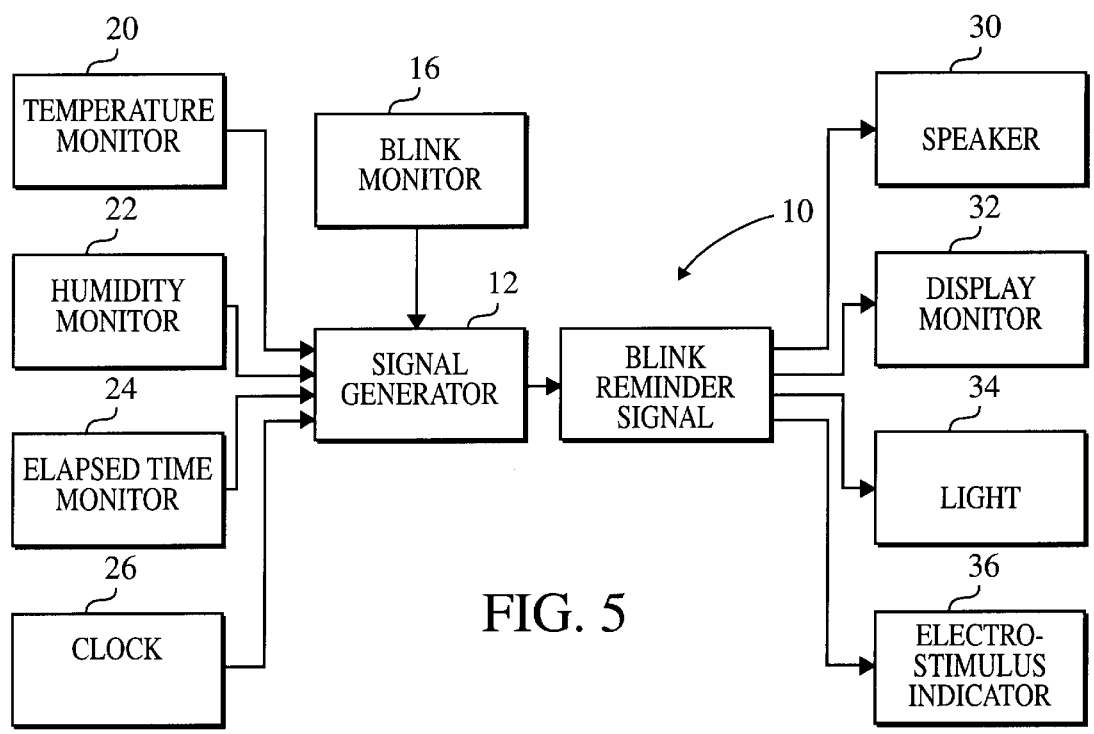
FIG. 5 is a schematic diagram of one aspect the present invention showing different types of blink indicators.

The blink indicator 14 in communication with the signal generator 12 interprets and communicates the blink reminder signal to the computer user 1 reminding the computer user 1 to blink. In general, the blink indicator 14 may be an audible indicator, a visual indicator, an electro-stimulus member 36, or some other indicator that provides a reminder to the computer user 1. FIG. 5 is a schematic diagram of the device 10 incorporating a number of different types of blink indicators 14.

As shown in the FIG. 5, the blink indicator 14 may comprise a speaker 30 in communication with the signal generator 12 adapted to produce an audible blink reminder. The audible blink reminder produced by the speaker 30 may be a simple tone or beep, an audible voice, or any other sound. In a system incorporating external inputs providing feedback to the signal generator 12, the audible blink reminder may be varied as needed to maintain the desired blink rate. For example, if the device 10 incorporates a blink monitor 16 that provides feedback of the computer user's blinks to the signal generator 12, the audible blink reminder may become louder or change pitch, a simple beep reminder may be modified to provide an audible voice reminder advising the computer user 1 to blink more to avoid CVS, or the blink reminder may comprise a song that increases or decreases in tempo according to the computer user's blinks. The possible variations of the audible blink reminder are numerous and anticipated.

An alternative blink reminder is a visible indicator adapted to produce a visual blink reminder. One visible indicator includes one or more lights 32 positioned and adapted for viewing by the computer user 1. As the computer user's blink rate changes, the frequency of light flashes may also be changed to help adjust the computer user's blink rate to the desired blink rate. Also the intensity or color of the light may change in response to the blink reminder signal.

Another possible visible indicator comprises at least a portion of the display monitor 34 used by the computer user 1. In this alternative embodiment, the visible indicator may be a simple dot on the display monitor 6, a specially designed character or icon that changes or moves, or a subliminal message formed of intermittent pixels designed to be seen only subliminally by the computer user 1. The number of possible variations are apparent as anything that may be shown on a display monitor 6 of a computer 5 may serve as a visible indicator and a visual blink reminder.

An additional embodiment for the blink indicator 14 comprises an electro-stimulus member 36 adapted to produce an electro-stimulus blink reminder. An electro-stimulus member 36 works by providing an electro-stimulus to the muscles that control the blinking motion of the computer user 1. The electro-stimulus creates an involuntary blinking response by the computer user 1 because it controls the muscles responsible for blinking. Therefore, the electro-stimulus member 36 ensures that the computer user 1 blinks according to the optimal blink rate.

The various blink indicators 14 may be selectively combined to provide multiple or varying blink reminders. Varying the blink reminders may provide a better system for helping the computer user 1 to blink at an appropriate rate and, thereby, maintain a proper preocular tear film 3 to avoid CVS.

Figure 6:
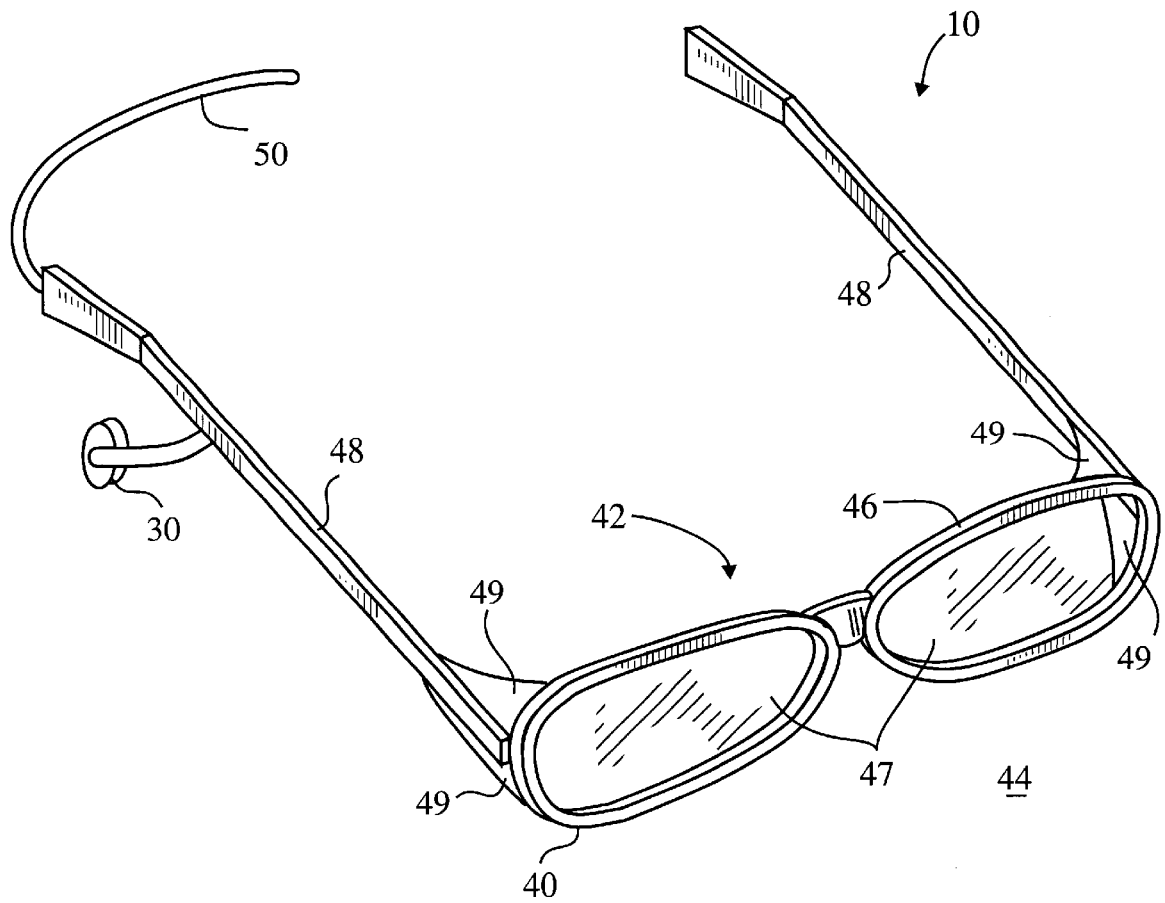
FIG. 6 is a perspective view of an eye enclosure.
Figure 9:
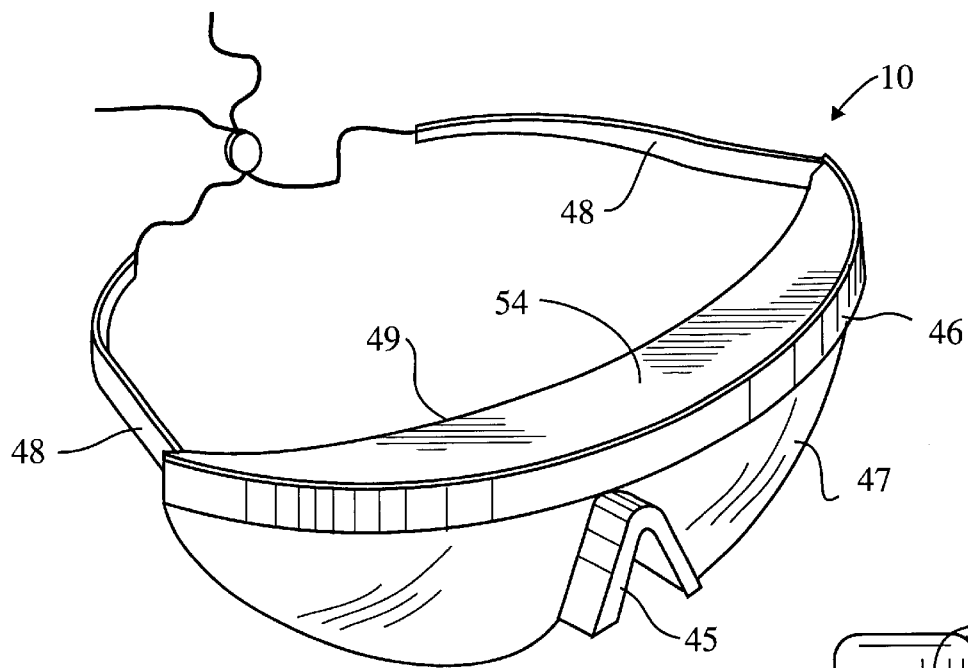
FIG. 9 is a perspective view of an eye enclosure.

Another aspect of the invention, shown in FIG. 6, provides an eye enclosure 40 adapted to provide an enclosed area 42 about the computer user's eyes 2 that is at least partially enclosed from the surrounding environment 44 without obstructing the computer user's vision, or view, of the display monitor 6 and provides means for supporting and maintaining the eye enclosure 40 on the computer user 1. FIGS. 6, 8, and 9 show three of the many possible designs for the eye enclosures 40. As used herein, the term "enclosed area 42 about the computer user's eyes 2" shall mean generally an area or volume proximal the eyes 2, eye lids, and eye sockets of the computer user 1, but external to the computer user's body. FIG. 6 is a perspective view of an eye enclosure 40 comprising a pair of spectacles having enclosure walls 49 that form an enclosure between the eye enclosure 40 and the computer user's face that partially enclose the enclosed area 42 from the surrounding environment 44. FIG. 8 shows an eye enclosure 40 adapted to fully enclose the enclosed area 42 between the eye enclosure 40 and the computer user's face from the surrounding area. FIG. 9 shows an alternative, preferred embodiment for the eye enclosure 40 that provides partial enclosure of the enclosed area 42. Each of the eye enclosures 40 are more fully discussed below.

Although the figures show some of the preferred embodiments for the invention, the number of alternative designs (particularly aesthetic changes) is virtually unlimited. For example, rather than merely enclosing the eyes, the eye enclosure 40 may comprise a full or partial helmet that fits over the computer user's head. In the case of a helmet, the display monitor may be incorporated into the forward shield of the helmet (a well-known device to those skilled in the art).

The eye enclosure 40 shown in FIG. 6 comprises a pair of spectacles having a frame 46 supporting a pair of lenses 47. The lenses 47 may be simple panes that do not affect the images passing therethrough or may be adapted to provide magnification of images to relieve the strain associated with eye accommodation. The lenses 47 may also be tinted or include other common spectacle lens 47 features to ease the strain on the eye. The frame 46 includes a pair of side arms 48 adapted and positioned to extend over the ears of the computer user 1 to support and maintain the eye enclosure 40 in position on the computer user 1. An enclosure wall 49 extending between portions of the frame 46, in particular between the frame portion supporting the lenses 47 and the side arms 48, provides for partial enclosure of the enclosed area 42, the area between the spectacles and the computer user's face. Preferably, the enclosure wall 49 is formed from a flexible material that will mold itself to the contours of the computer user's face and provide a seal between the spectacles and the computer user's face. By enclosing the environment about the computer user's eyes 2 from the surrounding environment 44 (i.e. creating an enclosed area 42), even when the area is only partially enclosed, the conditions of the enclosed area 42 can be manipulated to provide better, or optimal, environmental conditions for the computer user's eyes 2.

The eye enclosure 40 depicted in FIGS. 6 and 7 supports a small speaker 30 adapted and positioned to fit within the computer user's ear. The speaker 30 may be used to provide an audible blink reminder to the computer user 1 as previously described. A communication line 50 extends from the signal generator 12 to the eye enclosure 40 and communicates with the speaker 30 and any other equipment on the eye enclosure 40, such as a blink monitor 16 attached to the inside of the spectacle frame 46, to transmit power, information, and the blink reminder signal therebetween.

FIG. 7 is a partial perspective view of a computer user 1 operating a computer 5 and viewing the display monitor 6 of the computer 5. The computer user 1 is wearing an eye enclosure 40, similar to that shown in FIG. 6, that provides an enclosed area 42 that is partially enclosed. A communication line 50 extends from the computer 5 used by the computer user 1 to the eye enclosure 40 and communicates with any equipment on the eye enclosure 40, such as a blink monitor 16 attached to the inside of the spectacle frame 46, to transmit power and information therebetween. The computer 5 acts as the signal generator 12 and communicates with attached speakers 30 and the display monitor 6. The blink indicator 14 may therefore be the speakers 30 or a portion of the display monitor 34, as shown in the figure.

FIG. 8 shows an eye enclosure 40 adapted to fully enclose the enclosed area 42 (i.e. the area between the computer user's face and the eye enclosure 40). The eye enclosure 40 comprises a pair of goggles having a frame 46 supporting at least one lens 47. The lens 47 may be a simple pane that does not affect the images passing therethrough or may be adapted to provide magnification of images to relieve the strain associated with eye accommodation. The lenses 47 may also include a tinting or other common spectacle lens 47 features to ease the strain on the eye. An enclosure wall 49 formed of a flexible material extends from the frame 46 toward the computer user's face and is adapted to mold itself to the computer user's face to complete a tight seal about the full perimeter of the eye enclosure 40. In this way, the eye enclosure 40 provides a complete, or fully, enclosed area 42 about the computer user's eyes 2. A flexible, resilient support strap 52 extends between the opposing sides of the eye enclosure 40. The support strap 52 is adapted to stretch over the computer user's head and support and maintain the eye enclosure 40 in position on the computer user 1. The support strap 52 is preferably sufficiently resilient to hold the eye enclosure 40 tightly against the computer user's face to provide a better seal between the enclosure 40 and the user's face and to better seal the enclosed area 42 from the surrounding environment 44. The eye enclosure 40 is sufficiently large that it may be worn by the computer user 1 over the computer user's spectacles.

Filter members 54 positioned in the enclosure wall 49 of the eye enclosure 40 are in fluid communication with and allow limited airflow between the enclosed area 42 and the surrounding environment 44. The filter members 54 are adapted to filter the air passing into the enclosed area 42 to remove any smoke, pollen, other allergens, dust, or other particulate irritants from the air entering the enclosed area 42. Removing the particulate irritants eliminates one important environmental cause of eye irritation and reduces the likelihood of suffering from CVS. For example, the filter member 54 may be a high efficiency particulate accumulator (HEPA) filter or the like having filter cartridges that may be easily replaced.

Additionally, the eye enclosure 40 includes a pair of lights 32 mounted in the frame 46 that act as visible indicators, the operation of which is discussed above. However, in one alternative embodiment, the lens 47 of the eye enclosure 40 includes a slightly reflective lens 47 characteristic on the inner surface of the lens 47. Thus, when the lights 32, located within the enclosed area 42 and directed at the lens 47, flash to provide the visual blink reminder, the light is reflected off the internal, reflective surface of the lens 47 to the computer user's eye providing a relatively low intensity flash of light across the full view of the computer user's vision. Thus, the visual blink reminder is apparent regardless of where the computer user's eyes 2 are pointed.

FIG. 9 shows an alternative, preferred embodiment for the eye enclosure 40. In this embodiment, the lens 47 is curved and wraps partially around the computer users face to act as an enclosure wall 49 on the sides. An enclosure wall 49 extends the full width of the eye enclosure and is removably attached to the frame 46 above the lens 47. The removable enclosure wall 49 incorporates the filter member 54 providing greater flexibility for the eye enclosure 40. Also, the nose piece 45 is removable.

People's faces are not all shaped the same. Some have more pronounced noses while others have relatively flat noses. By providing a removable nosepiece 45, the user may select the nosepiece best suited to their face. In this way, the nosepiece may be selected to provide a better seal between the eye enclosure 40 and the computer user's face providing a better seal for the enclosed area 42.

Once the enclosed area 42 is established by the eye enclosure 40, the environmental conditions within the enclosed area 42 may be manipulated to provide an optimum, or near optimum, environment for the eyes 2. One important condition to control within the enclosed area 42 is the moisture in the air (i.e. the humidity). Accordingly, the device 10 preferably incorporates means for moistening the enclosed area 42 (also referred to herein as the "air moistener"). In general, the air moistener may comprise any one of a number of possible embodiments shown in FIGS. 8. 10, 11, 14A and 14B including a nebulizer 60, additional moistening fluid 82 (such as a hyperosmotic fluid) applied to the computer user's eyes 2 themselves, an eye insert that slowly dissolves into the cul de sac of the eye and alters the properties of the tear film, or a moistening fluid supply 66 communicating with the enclosed area 42 and adapted to allow the moistening fluid 82 to evaporate into the enclosed area 42.

The device 10 shown in FIG. 8 incorporates a nebulizer 60. The nebulizer 60 is attached to the eye enclosure 40 and is in fluid communication with the enclosed area 42. The nebulizer 60 is adapted to provide a supply of nebulized moistening fluid 82 to the enclosed area 42.

FIG. 8 shows a portable base unit 62 connected to and in communication with the eye enclosure 40. The portable base unit 62 comprises a separate control member 64, that serves as the signal generator 12, and a moistening fluid supply 66. A communication line 50 extends from the portable base unit 62 to the eye enclosure 40 and communicates with the lights 32 and any other equipment on the eye enclosure 40, such as a blink monitor 16 attached to the inside of the frame 46, to transmit power, information, and the blink reminder signal therebetween. The control member 64 of the portable base unit 62 includes adjustment members 68 and display members 70 that allow the computer user 1 to monitor and control the blink reminder signal, the nebulizer 60, and the environmental conditions of the device 10.

The portable base unit 62 includes a removable fill cap 72 that allows the computer user 1 to selectively fill the moistening fluid supply 66 and a view port 74 that allows the computer user 1 to track the amount of moistening fluid 82 in the moistening fluid supply 66. A pump member 75 within the portable base member directs the moistening fluid 82 through a fluid communication line 50 to the eye enclosure 40. The frame 46 of the eye enclosure 40 includes fluid passageways therein that direct the moistening fluid 82 to the nebulizer 60 to spray the nebulized moistening fluid 82 into the enclosed area 42. The control member 64 is adapted to control the rate and amount of nebulized moistening fluid 82 sent to the enclosed area 42. Thereby, the nebulizer 60 provides an air moistener for the device 10.

Figure 10:
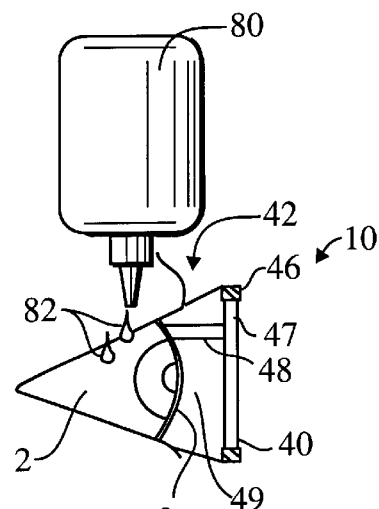
FIG. 10 is a schematic view of one type of air moistener.
Figure 11:
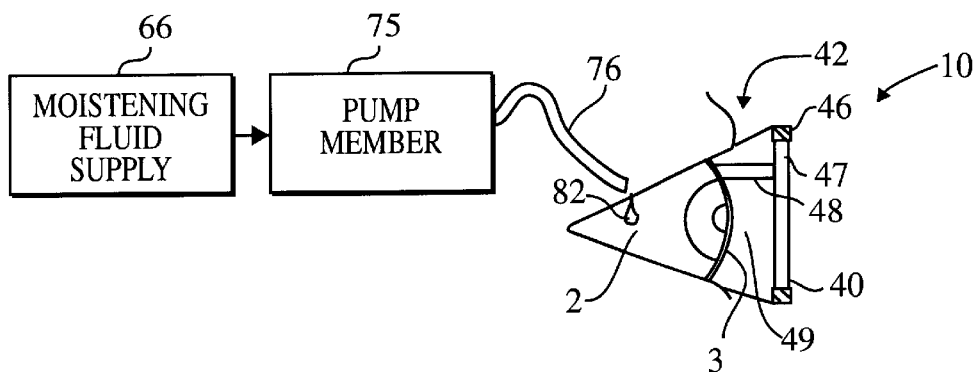
FIG. 11 is a schematic view of an air moistener that uses a pump member to deliver the moistening fluid to the computer user's eyes.

A second air moistener comprises a moistening fluid 82 applied to the computer user's eyes 2 so that the moistening fluid 82 evaporates from the eyes 2, which acts as a fluid reservoir, and moistens the enclosed area 42. FIGS. 10 and 11 show two of the possible embodiments for this type of air moistener. FIG. 10 is a schematic drawing showing an eyedropper 80 of moistening fluid 82 being used to manually apply moistening fluid 82 to the computer user's eye. The eye is partially enclosed by the eye enclosure 40 creating an enclosed area 42. Once the moistening fluid 82 is applied to the computer user's eye it evaporates, moistening the air in the enclosed area 42.

Likewise, FIG. 11 is a schematic drawing showing an automated moistening fluid 82 delivery system. In this embodiment, the device 10 includes a moistening fluid supply 66 in fluid communication with a pump member 75. The pump member 75 is adapted to pump the moistening fluid 82 from the moistening fluid supply 66 through a communication line 50, in fluid communication therewith, and to the computer user's eyes 2. The communication line 50 is positioned and adapted to direct the fluid to the computer user's eyes 2 and may include a nozzle to accelerate the moistening fluid 82 and propel it to the eyes 2.

Figure 12:
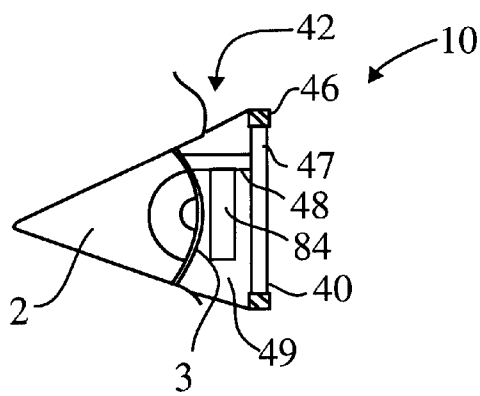
FIG. 12 is a schematic view of an air moistener using a liquid permeable member.

An alternative embodiment for the air moistener comprises a moistening fluid supply 66 of moistening fluid 82 in fluid communication with the enclosed area 42. The moistening fluid supply 66 is adapted to permit evaporation of the moistening fluid 82 from the moistening fluid supply 66 into the enclosed area 42. One embodiment for this air moistener is shown in FIG. 12 and comprises a liquid permeable member 84, such as a sponge, adapted to absorb the moistening fluid 82 and permit evaporation of the moistening fluid 82. The liquid permeable member 84 is attached to the frame 46 and the enclosure wall 49 of the eye enclosure 40 within the enclosed area 42. The computer user 1 simply applies the moistening fluid 82 to the liquid permeable member 84 before putting on the eye enclosure 40. Once in place, the moistening fluid 82 evaporates from the liquid permeable member 84 moistening the air in the enclosed area 42.

Figure 13:
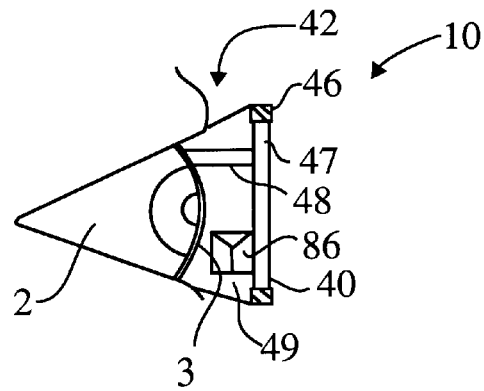
FIG. 13 is a schematic view of an air moistener using an open reservoir.

Another embodiment for this air moistener is shown in FIG. 13 and comprises an open reservoir 86 containing moistening fluid 82. The open reservoir is attached to the frame 46 and the enclosure wall 49 of the eye enclosure 40 within the enclosed area 42. The computer user 1 places the moistening fluid 82 within the reservoir 86 before putting on the eye enclosure 40. Once in place, the moistening fluid 82 evaporates from the reservoir 86 into the enclosed area 42 moistening the air.

Each of the described embodiments for the air moistener is provided to increase the moisture in the enclosed area 42 and reduce the effects of evaporation from the eye. Reducing the evaporation, helps to maintain a proper and sufficient preocular tear film 3 which is a major cause of CVS.

To further reduce the likelihood of suffering from CVS, the moistening fluid 82 used may be adapted according to the needs of the individual computer user 1. Computer users may suffer from different types of CVS in that some experience ocular complaints at different times than others and experience different types of ocular complaints from others. Some of these symptoms may relate to the composition of the tear film 3. The deficiencies in tear film 3 may often be determined by examining the symptoms of the computer user 1. Thus, once the deficiency is determined, the moistening fluid 82 may be adapted to the needs of the computer user 1. For a computer user 1 having an aqueous deficiency, the moistening fluid 82 may be a preservative free aqueous; for a computer user 1 having a mucin deficiency, the moistening fluid 82 may be a topical mist of a goblet cell secreting agent such as bromhexine; and for a computer user 1 having a lipid deficiency, the moistening fluid 82 may be a micron drop of ocular oil. Providing a moistening fluid 82 according to the needs of the individual helps to better avoid CVS.

Thus, often the problem of maintaining an adequate tear film 3 is caused by the composition of the tear film 3 or may be solved by altering the composition or characteristics of the tear film 3. Adding one or more of the above-mentioned agents to the moistening fluid 82 provides one manner of changing the characteristics of the tear film 3. In addition to adding these agents, the moistening fluid 82 may contain other agents that modify the tear film 3 in other ways. For example, the moistening fluid preferably has colligative properties that increase the absorptive characteristics of the tear film 3 and reduce the evaporative characteristics of the tear film 3 comprising a hyperosmotic substance. Providing a hyperosmotic substance in the moistening fluid 82 increases the stability of the tear film 3 by attracting more moisture to the eye 2 and reducing the amount of moisture evaporating from the eye 2.

Figure 14A:
FIG. 14A is a side elevational view of a pellet.
Figure 14B:
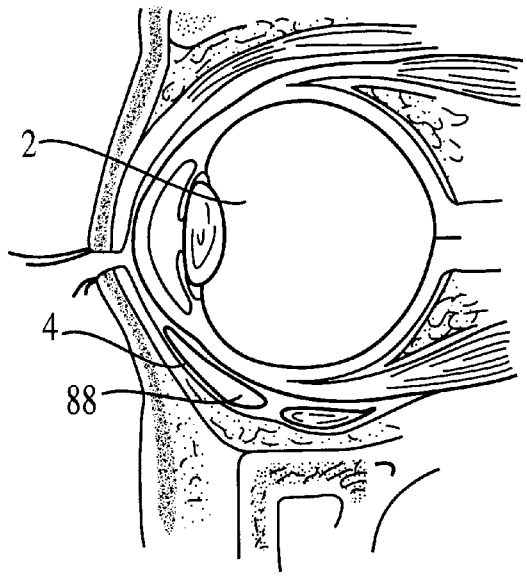
FIG. 14B is a cross sectional view of an eye having a pellet positioned in the cul de sac.

In an alternative embodiment, rather than providing the agents in the form of a moistening fluid, a small pellet 88 supplies the desired agents. FIG. 14A is an elevational view of a pellet 88. FIG. 14B shows the pellet 88 positioned in the computer user's eye 2. The pellet 88 is sized and adapted to fit in the cul de sac 4 of the computer user's eye 2. Preferably, the pellet 88 has a tear-drop-like shape so that it conforms to the shape of the cul de sac. Once placed in the cul de sac 4 and exposed to the natural eye fluid, the pellet 88 slowly dissolves and releases a substance into the computer user's cul de sac 4. Through blinking and diffusion, the substance spreads throughout the tear film 3 and becomes mixed with the tear film 3. The substance is adapted to alter the characteristics of the tear film 3 and may include the substances previously mentioned (e.g. a preservative free aqueous, an ocular oil, a goblet cell secreting agent, a hyperosmotic substance) or other useful substances. Because the pellet 88 dissolves slowly, a single pellet 88 can be used to control or alter the tear film characteristics for an extended period of time. Also, the pellet may be used in combination with moistening fluid 82 to better moisten the eye 2.

Figure 15:
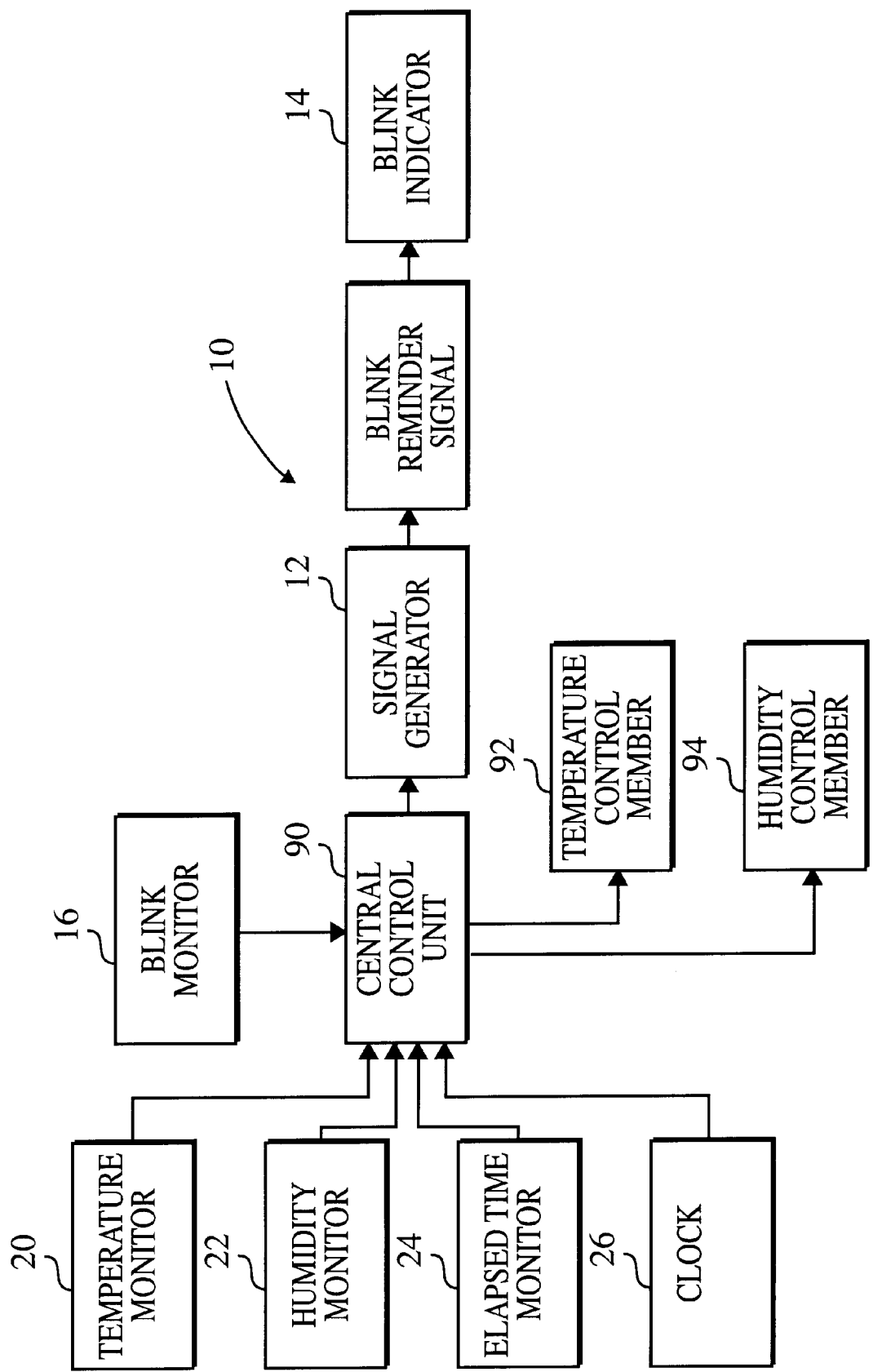
FIG. 15 is a schematic diagram of the present invention showing different devices used to monitor and control the environmental conditions in the enclosed area.

The environment about the computer user's eyes 2, the enclosed area 42, may be further controlled to provide an optimal eye environment to avoid CVS. FIG. 15 is a schematic diagram showing additional components of the device 10 aimed at controlling the eye environment. The components include means for monitoring and adjusting the temperature of the enclosed area 42 to maintain a predetermined temperature in the enclosed area 42 and means for monitoring and adjusting the humidity of the enclosed area 42 to maintain a predetermined humidity of the enclosed area 42. The device 10 shown in FIG. 15 includes a central control unit 90, which may be the computer 5 used by the computer user 1 or a separate control unit. A temperature monitor 20 and a humidity monitor 22 adapted and positioned to monitor the temperature and humidity respectively of the enclosed area 42 are in communication with the central control unit 90 and provide the temperature and humidity information thereto. The central control unit 90 is preprogrammed with the desired temperature and humidity. As the temperature or humidity varies from the preprogrammed values or value ranges, the central control unit 90 activates the temperature control member 92 and the humidity control member 94 as needed. The temperature control member 92 may comprise small resistance type heaters mounted in the frame 46 of the eye enclosure 40 and positioned and insulated to avoid injury. The humidity control member 94 may comprise one of the air moisteners previously described. For example, the humidity control member 94 may comprise a nebulizer 60 with the central control unit 90 directing the flow rate of the nebulized moistening fluid 82. As the temperature and humidity are interrelated, the control member is adapted to adjust the environmental conditions as needed to optimize the eye environment within the enclosed area 42.

Other components of the present invention aimed at reducing or eliminating the causes of CVS include relaxing the facial muscles and adjusting the workplace ergonomics. Tense muscles may contribute to CVS. The muscles (e.g. periorbital muscle, masseter muscle, facial muscles, temporalis muscle) may be massaged, injected with a relaxant, or have a skin applied relaxant such as a botulinum toxin placed thereon to relieve the tension and reduce the effects of CVS.

Ergonomic factors may also be used to reduce the effects of CVS. For example, lowering the display monitor 6 so that the computer user 1 looks down reduces the size of the eye opening and, thereby, reduces the evaporation of tear film. Other ergonomic factors may help to reduce the effects of CVS.

While the foregoing is directed to the preferred embodiment of the present invention, other and further embodiments of the invention may be devised without departing from the basic scope thereof, and the scope thereof is determined by the claims which follow.

I claim:

1. A method for preventing computer vision syndrome in a user viewing a display monitor, comprising:

generating a blink reminder signal:

indicating a blink reminder to the user in response to the blink reminder signal; and placing a pellet sized and adapted to fit in the cul de sac of an eye of the user, the pellet adapted to dissolve and release a substance into tear film of said eye.

2. A method for preventing computer vision syndrome in a user viewing a display monitor, comprising:

generating a blink reminder signal;

indicating a blink reminder to the user in response to the blink reminder signal; and increasing the absorptive and decreasing the evaporative characteristics of a preocular tear film of an eye of the user.

3. An apparatus for preventing computer vision syndrome in a user viewing a display monitor, comprising:

an eye enclosure adapted to provide an enclosed area about the eyes of the user that is at least partially enclosed from a surrounding environment without obstructing vision by the user of the display monitor;

means for supporting and maintaining the eye enclosure in position on the user; and a filter member attached to the enclosure, wherein the filter member is in fluid communication with the enclosed area and the surrounding environment.

4. The apparatus as claimed in claim 3, wherein the eye enclosure adapted to provide an enclosed area about the computer user's eyes fully encloses said area from a surrounding environment.

5. The apparatus as claimed in claim 3, further comprising at least one removable nosepiece so that the nosepiece may be selected according to the shape of the face of the user.

6. The apparatus as claimed in claim 3, further comprising means for moistening the enclosed area.

7. The apparatus as claimed in claim 6, wherein the means for moistening the enclosed area comprises:

a nebulizer attached to the eye enclosure; and the nebulizer is in fluid communication with the enclosed area and adapted to provide a supply of nebulized moistening fluid to the enclosed area.

8. The apparatus as claimed in claim 6, wherein the means for moistening the enclosed area comprises a moistening fluid applied to one or more eyes of the user so that the moistening fluid evaporating from said eyes moistens the enclosed area.

9. The apparatus as claimed in claim 6, wherein the means for moistening the enclosed area is adapted to provide a preservative free aqueous to the enclosed area.

10. The apparatus as claimed in claim 6, wherein the means for moistening the enclosed area is adapted to provide goblet cell secreting agents to the enclosed area.

11. The apparatus as claimed in claim 6, wherein the means for moistening the enclosed area is adapted to provide a bromhexine to the enclosed area.

12. The apparatus as claimed in claim 6, wherein the means for moistening the enclosed area is adapted to provide a hyperosmotic substance to the enclosed area.

13. The apparatus as claimed in claim 6, wherein the means for moistening the enclosed area is adapted to provide an ocular oil to the enclosed area.

14. The apparatus as claimed in claim 3, wherein the filter member is a high efficiency particulate accumulator filter.

15. The apparatus as claimed in claim 3, wherein the filter member is removably attached to the enclosure.

16. The apparatus as claimed in claim 3, further comprising:

a lens member attached to the eye enclosure; and the lens member adapted and positioned to provide magnification of images seen by the eyes of the user.

17. The apparatus as claimed in claim 16, wherein the lens member is tinted.

18. The apparatus as claimed in claim 3, wherein the eye enclosure is sized and adapted to fit over a pair of spectacles worn by the user.

19. An apparatus for preventing computer vision syndrome in a user viewing a display monitor, comprising:

an eye enclosure adapted to provide an enclosed area about the eyes of the user that is at least partially enclosed from a surrounding environment without obstructing vision by the user of the display monitor;

means for supporting and maintaining the eye enclosure in position on the user;

means for moistening the enclosed area;

a moistening fluid supply;

a pump member in fluid communication with the moistening fluid supply;

a communication line in fluid communication with the pump member, the communication line positioned and adapted to direct the moistening fluid to the, eyes wherein the pump member is adapted to pump the moistening fluid from the moistening fluid supply, through the communication line, and to the eyes.

20. An apparatus for preventing computer vision syndrome in a user viewing a display monitor, comprising:

an eye enclosure adapted to provide an enclosed area about the eyes of the user that is at least partially enclosed from a surrounding environment without obstructing vision by the user of the display monitor;

means for supporting and maintaining the eye enclosure in position on the user; and means for moistening the enclosed area, wherein the means for moistening the enclosed area comprises a moistening fluid supply of a moistening fluid in fluid communication with the enclosed area, wherein the moistening fluid supply is adapted to permit evaporation of the moistening fluid from the moistening fluid supply to the enclosed area.

21. The apparatus as claimed in claim 20, wherein the moistening fluid supply comprises an open reservoir.

22. The apparatus as claimed in claim 20, wherein the moistening fluid supply comprises a liquid permeable member adapted to absorb the moistening fluid and permit evaporation therefrom.

23. An apparatus for preventing computer vision syndrome in a user viewing a display monitor, comprising:

an eye enclosure adapted to provide an enclosed area about the eyes of the user that is at least partially enclosed from a surrounding environment without obstructing the vision by the user of the display monitor;

means for supporting and maintaining the eye enclosure in position on the user;

means for moistening the enclosed area; and means for monitoring an environmental condition of the enclosed area.

24. The apparatus as claimed in claim 23, further comprising means for adjusting the environmental condition of the enclosed area adapted to maintain a predetermined environmental condition in the enclosed area.

25. The apparatus as claimed in claim 23, wherein the environmental condition is temperature or humidity.

26. An apparatus for preventing computer vision syndrome in a user viewing a display monitor, comprising:

an eye enclosure adapted to provide an enclosed area about the eyes of the user that is at least partially enclosed from a surrounding environment without obstructing the vision by the user of the display monitor;

means for supporting and maintaining the eye enclosure in position on the user; and a pellet sized and adapted to fit in the cul de sac of an eye of the user wherein;

the pellet is adapted to dissolve and release a substance into a tear film that alters the characteristics of the tear film of the user.

27. The apparatus as claimed in claim 24, wherein the substance released by the pellet increases the absorption and decreases the evaporation of the tear film.

28. The apparatus as claimed in claim 24, wherein the substance released by the pellet is a hyperosmotic substance.

29. The apparatus as claimed in claim 26, wherein the substance released by the pellet provides a preservative free aqueous.

30. The apparatus as claimed in claim 26, wherein the substance released by the pellet provides an ocular oil.

31. The apparatus as claimed in claim 26, wherein the substance released by the pellet provides a goblet cell secreting agent.

32. The apparatus as claimed in claim 26, wherein the pellet has a tear-drop-like shape.

33. A method for preventing computer vision syndrome in a user viewing a display monitor, comprising:

providing an eye enclosure adapted to provide an enclosed area about the eyes of the user that is at least partially enclosed without obstructing the vision by the user of the display monitor;

supporting and maintaining the eye enclosure in position on the; and filtering the air entering the enclosed area.

34. The method as claimed in claim 33, further comprising fully enclosing the eyes of the user.

35. The method as claimed in claim 33, further comprising moistening the enclosed area.

36. The method as claimed in claim 35, further comprising:

applying the moistening fluid to eyes; and allowing the moistening fluid to evaporate from the eyes.

37. The method as claimed in claim 35, further comprising:

providing a moistening fluid supply of a moistening fluid in communication with the enclosed area, the moistening fluid supply adapted to permit evaporation of the moistening fluid from the moistening fluid supply to the enclosed area; and allowing the moistening fluid to evaporate from the moistening fluid supply.

38. The method as claimed in claim 33, further comprising reducing the light entering the eyes of the user by tinting the eye enclosure.

39. A method for preventing computer vision syndrome in a user viewing a display monitor comprising:

providing an eye enclosure adapted to provide an enclosed area about the eyes of the user that is at least partially enclosed without obstructing the vision by the user of the monitor;

supporting and maintaining the eye enclosure in position on the user;

moistening the enclosed area, wherein moistening comprises nebulizing a moistening fluid; and spraying the nebulized moistening fluid into the enclosed area.

40. A method for preventing computer vision syndrome in a user viewing a monitor, comprising:

providing an eye enclosure adapted to provide an enclosed area about the eyes of the user that is at least partially enclosed without obstructing vision of the monitor;

supporting and maintaining the eye enclosure in position on the user;

placing a pellet sized and adapted to fit in the cul de sac of an eye of the user, the pellet adapted to dissolve and release a substance into a tear film of the user that alters the characteristics of the tear film.

41. A method for preventing computer vision syndrome in a user viewing a display monitor, comprising:

providing an eye enclosure adapted to provide an enclosed area about the eyes of the user that is at least partially enclosed without obstructing vision of the display monitor;

supporting and maintaining the eye enclosure in position on the user;

increasing the absorptive and decreasing the evaporative characteristics of the preocular tear film of the user.

42. The method as claimed in claim 41, further comprising:

monitoring the temperature of the enclosed area; and adjusting the temperature of the enclosed area to maintain a predetermined temperature.

43. The method as claimed in claim 41, further comprising:

monitoring the humidity of the enclosed area; and adjusting the humidity of the enclosed area to maintain a predetermined humidity.

44. The method as claimed in claim 41, further comprising:
- adapting a moistening fluid to the specific needs of the user; and
- using the moistening fluid to moisten the enclosed area.

45. The method as claimed in claim 44, further comprising:
- using a preservative free aqueous as the moistening fluid for the user suffering from aqueous deficiency;
- applying a bromhexine as the moistening fluid for the user suffering from mucin deficiency; and
- applying an oil as the moistening fluid for the user suffering from lipid deficiency.

46. A system for preventing computer vision syndrome in a user viewing a display monitor, comprising:
- an eye enclosure adapted to provide an enclosed area about the eyes of the user that is at least partially enclosed from a surrounding environment without obstructing the vision by the user of the display monitor;
- means for supporting and maintaining the eye enclosure in position on the user;
- means for moistening the enclosed area;
- means for generating a blink reminder signal; and
- means for indicating a blink reminder to the user in response to the blink reminder signal.

47. The system as claimed in claim 46, further comprising:
- a lens member attached to the eye enclosure;
- an inner surface of the lens member having reflective characteristics;
- the means for indicating a blink reminder comprising a light attached to the eye enclosure and positioned within the enclosed area wherein a portion of the light reflects on the inner surface of the lens to provide the blink reminder to the user.

48. An apparatus for reducing the effects of computer vision syndrome in a user, comprising:
- a pellet sized and adapted to fit in the cul de sac of an eye of the user; wherein
- the pellet is adapted to dissolve and release a substance into a tear film of the eyes of the user that alters the characteristics of the tear film.

49. The apparatus as claimed in claim 48, wherein the substance released by the pellet increases the absorption and decreases the evaporation of the tear film.

50. The apparatus as claimed in claim 48, wherein the substance released by the pellet is a hyperosmotic substance.

51. The apparatus as claimed in claim 48, wherein the substance released by the pellet provides a preservative free aqueous.

52. The apparatus as claimed in claim 48, wherein the substance released by the pellet provides an ocular oil.

53. The apparatus as claimed in claim 48, wherein the substance released by the pellet provides a goblet cell secreting agent.

54. The apparatus as claimed in claim 48, wherein the pellet has a tear-drop-like shape.

55. The apparatus as claimed in claim 48, wherein the pellet has a shape that is similar to the shape of an eye cul de sac.

* * * * *